United States Patent [19]

Dachs, deceased et al.

[11] 4,359,590

[45] Nov. 16, 1982

[54] TITANATE ESTER-STABILIZED BISPHENOLS

[75] Inventors: Norman W. Dachs, deceased, late of Buffalo, N.Y., by Georgianna M. Dachs, executrix; James W. Ginter; Joseph A. Pawlak, both of Cheektowaga, N.Y.

[73] Assignee: Occidental Chemical Corporation, Niagara Falls, N.Y.

[21] Appl. No.: 262,377

[22] Filed: May 11, 1981

[51] Int. Cl.$^3$ ............................................. C07C 37/70
[52] U.S. Cl. .................................. 568/702; 568/701; 568/703
[58] Field of Search ............... 568/703, 728, 701, 702, 568/717

[56] References Cited

U.S. PATENT DOCUMENTS 4,126,602 11/1978 Sales ................................ 260/40 R

FOREIGN PATENT DOCUMENTS 820960 9/1959 United Kingdom ............... 568/703
890432 2/1962 United Kingdom .
924607 4/1964 United Kingdom .
1022583 3/1966 United Kingdom .

OTHER PUBLICATIONS

Kirk-Orthmer, "Encyclopedia of Chemical Tech.", vol. 20, pp. 451-457, (1963), 2nd ed.

*Primary Examiner*—Werren B. Lone
*Attorney, Agent, or Firm*—J. F. Tao; J. F. Mudd

[57] ABSTRACT

A bisphenol is stabilized against thermal decomposition in the molten state in a non-reactive environment by incorporation in the bisphenol of a small stabilizing amount of a quaternary ester of ortho titanic acid and an aliphatic alcohol.

27 Claims, No Drawings

TITANATE ESTER-STABILIZED BISPHENOLS

This invention relates to stabilized phenolic compositions, and more particularly to bisphenol compositions stabilized against thermal decomposition in the molten state.

BACKGROUND OF THE INVENTION

Bisphenols in the molten condition, at elevated temperatures in the range of above about 100° to about 350° C. or higher, i.e. 400° C., are known to decompose to form, in general, simpler phenolic substances i.e. monohydroxy phenols, such as phenol together with other decomposition products such as monohydroxy phenols containing an ethylenically unsaturated aliphatic side chain, i.e. alkenyl phenols.

For example, bisphenol A, i.e. 2,2-(4,4'dihydroxy diphenyl) propane, is known to decompose on heating to form equimolar proportions of phenol and p-isopropylidene phenol.

On further heating, the aforementioned thermal decomposition products of bisphenols, particularly the aforementioned phenol product containing an aliphatic unsaturated substituent can, form complex non-volatile compounds.

The above-described thermal decomposition products of the bisphenols, even in small concentrations, have an adverse effect on compositions, particularly polymers, e.g. linear aromatic polyesters, prepared from the bisphenols. In polyesters, for example, the adverse effect of the aforementioned decomposition product impurities include lowering of the polyester molecular weight.

Since the exact mechanism of thermal decomposition of bisphenol in a non-reactive environment for the bisphenol is complex and is not known with certainty, the selection of suitable bisphenol thermal stabilizer agents has been particularly empirical. For example, British Pat. No. 890,432, to Farbenfabriken Bayer, discloses secondary and tertiary alkaline earth phosphates, stannous oxalate, tin powder, mixtures of tin dioxide and tin powder, terephthalic acid, isophthalic acid, oxalic acid, adipic acid, sebacic acid, boron trioxide, antimony trioxide or mixtures thereof as stabilizer additives for molten bisphenols.

Also British Pat. No. 1,022,583, to Monsanto Corporation, discloses the aforementioned oxalic acid as stabilizer and additionally discloses citric acid, tartaric acid or alkali metal or ammonium salts of the foregoing acids as bisphenol stabilizer additives.

British Pat. No. 924,607, of B. E. Jennings, issued Apr. 24, 1963, assigned to Imperial Chemicals Industries, Ltd. teaches addition of an aliphatic titanate ester such as tetra n-butyl titanate, to mixtures of bisphenol and a dicarboxylic acid diaryl ester to catalyze transesterification polymerization of the mixtures to linear aromatic polyester of the bisphenol and dicarboxylic acid. This patent does not teach addition of the titanate ester to the bisphenol as stabilizer or teach bisphenol-titanate ester mixtures in a non-reactive environment for the bisphenol.

SUMMARY OF THE INVENTION

The invention provides bisphenol compositions stabilized effectively against thermal decomposition in the molten state which comprise a bisphenol and a small stabilizing amount of a quaternary ester of ortho titanic acid, and an aliphatic monohydroxy or polyhydroxy alcohol, which is devoid of an amino-substituent, i.e. a primary, secondary or tertiary amino group.

By quaternary ester of ortho-titanic acid is meant an ester of ortho titanic acid, namely $H_4TiO_4$, i.e. the oxy acid of titanium in a positive oxidation state of four, wherein all four hydrogens of the acid are replaced with organic groups of the hydroxy compound.

The stabilization of bisphenol with the titanate ester additive of the invention is achieved in absence of any other reagent known to react with the molten bisphenol, i.e. is achieved in a non-reactive environment for the bisphenol.

Use of the titanate ester thermal stabilizer additive of the invention in a bisphenol effectively inhibits decomposition of the bisphenol to simpler phenolic decomposition products, e.g. phenol, as is indicated by the results of Examples 1–4 compared in the Table below.

DETAILED DESCRIPTION OF THE INVENTION AND PREFERRED EMBODIMENTS THEREOF

The bisphenols which can be employed as the bisphenol substrate in the present compositions are known in the art and correspond to the general formula:

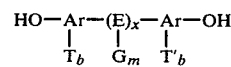

wherein Ar is aromatic, preferably containing 6–18 carbon atoms (including phenyl, biphenyl and naphthyl); G is alkyl, haloalkyl, aryl, haloaryl, alkylaryl, haloalkylaryl, arylalkyl, haloarylalkyl, cycloalkyl, or halocycloalkyl; E is a divalent (or di-substituted) alkylene, haloalkylene, cycloalkylene, halocycloalkylene, arylene, or haloarylene, —O—, —S—, —SO—, —SO$_2$—, —SO$_3$—, —CO—,

or GN<; T and T' are independently selected from the group consisting of halogen, such as chlorine or bromine, G and OG; m is an integer from 0 to the number of replaceable hydrogen atoms on E; b is an integer from 0 to the number of replaceable hydrogen atoms on Ar, and x is 0 or, preferably, 1. When there is plurality of G substituents in the bisphenols, such substituents may be the same or different. The T and T' substituents may occur in the ortho, meta or para-positions with respect to the hydroxyl radical. The foregoing hydrocarbons radicals preferably have carbon atoms as follows: alkyl, haloalkyl, alkylene and haloalkylene of 1 to 14 carbons; aryl, haloaryl, arylene and haloarylene of 6 to 14 carbons; alkylaryl, haloalkylaryl, arylalkyl and haloarylalkyl of 7 to 14 carbons; and cycloalkyl, halocycloalkyl, cycloalkylene and halocycloalkylene of 4 to 14 carbons. If desired, mixtures of the above described bisphenols may be employed as the bisphenol substrate. The bisphenols generally contain 12 to about 30 carbon atoms, and preferably 12 to about 25 carbon atoms.

Typical examples of bisphenols having the foregoing formula include bisphenol-A [i.e. bis(4-hydroxyphenyl)-2,2-propane], bis(3-hydroxyphenyl)-1,2-ethane, bis(4-hydroxyphenyl)-1,2-ethane, as well as the other bisphenols illustrated in G. Salee, U.S. Pat. No. 4,126,602 (issued Nov. 21, 1978) at Column 2, line 68 to Column 3, line 47, the disclosure of said patent being incorporated herein by reference.

Suitable biphenols are p,p'-biphenol and the other biphenols illustrated in the aforementioned U.S. Pat. No. 4,126,602 at Column 3, lines 47-55. Mixture of isomers of the foregoing bisphenols and biphenols can be used. Preferably the bisphenol of the present stabilized bisphenol composition is derived from bisphenol-A.

The aliphatic titanate esters stabilizer additives of the invention are known compounds which can be prepared by known preparatory techniques, e.g. by reaction of an alcohol containing 1, 2 or more hydroxy substituents with a halide, e.g. a chloride or bromide, especially a chloride, of titanium in a positive oxidation state of IV, for example titanium tetrachloride. The aforementioned aliphatic titanate esters and their preparation are more particularly described in Kirk-Othomer, *Encyclopedia of Chemical Technology*, 2nd Rev. Ed., Volume 20, 1968, John Wiley & Son, pages 451-470, the disclosure of which is incorporated herein by reference and in the bulletin entitled "Versatile Tyzor Organic Titanate", published by DuPont de Nemours Inc., the disclosure of which is also incorporated herein by reference.

In general the titanate ester additive of the invention is derived from an aliphatic hydroxy compound. In general, the aliphatic group of said hydroxy compound contains 1 to 12, preferably 1 to 8 carbon atoms. The aliphatic group can be acyclic, i.e. open chain, or cyclic in nature. Preferably, however, the titanate ester stabilizer of the invention is derived from an acyclic aliphatic hydroxy compound. When an acyclic aliphatic titanate ester is employed the aliphatic group can be straight chain or branched. The aliphatic group is desirably saturated.

It is preferred that the aliphatic group of the titanate ester stabilizer be a hydrocarbon aliphatic group i.e. derived from hydrogen and carbon atoms exclusively, although aliphatic titanate esters derived from substituted aliphatic hydroxy compounds can be employed. For example, suitable titanate esters of substituted aliphatic hydroxy compounds include titanate esters derived from halogen-substituted aliphatic hydroxy compounds; titanate esters derived from aliphatic hydroxy compounds containing aromatic substituents, e.g. aryl substituents of the benzene or naphthalene series and titanate esters derived from aliphatic hydroxy compounds containing lower alkoxy substituents, i.e. alkoxy substituents of 1 to 8 carbon atoms.

Titanate esters derived from aliphatic hydroxy compounds containing one, two, three or more hydroxy groups can be employed in the practice of the invention. However, it is generally preferred to employ a titanate ester of a mono- or di-hydroxy aliphatic compound, especially a monohydroxy alcohol.

The hydroxy group of the aliphatic hydroxy component of the ester can be a primary, secondary or tertiary hydroxy group. Conveniently, the hydroxy group is a primary hydroxy group when the ester is derived from a monofunctional alcohol.

The following are illustrative examples of titanate esters derived from aliphatic hydroxy components suitable for use as the stabilizer additive of the invention.

tetra-methyl titanate, $Ti(OCH_3)_4$
tetra-ethyl titanate, $Ti(OC_2H_5)_4$
tetra-n-propryl titanate, $Ti(OCH_2CH_2CH_3)_4$
tetra-isopropyl titanate, $Ti(OCH(CH_3)_2)_4$
tetra-isobutyl titanate, $Ti(OCH_2CH(CH)_3)_2)_4$
tetra-sec-butyl titanate, $Ti(O(CH_3)CHC_2H_5)_4$
tetra-tert-butyl titanate, $Ti(OC(CH_3)_3)_4$
mono n-butyl, trimethyl titanate, $Ti(OCH_3)_3(OC_4H_9)$
mono ethyl tricyclohexyl titanate, $Ti(OC_2H_5)(OC_6H_{11})_3$
tetra-n-amyl titanate
tetra-n-hexyl titanate
tetra-cyclopentyl titanate
tetra-cyclohexyl titanate
tetra-n-decyl titanate
tetra n-dodecyl titanate
tetra (2-ethyl hexyl) titanate
tetra octylene glycol titanate ester
tetrapropylene glycol titanate ester
tetra benzyl titanate
tetra-p-chloro benzyl titanate
tetra 2-chloroethyl titanate
tetra 2-bromoethyl titanate
tetra 2-methoxyethyl titanate
tetra 2-ethoxyethyl titanate Mixtures of these and equivalent titanate esters can also be employed in the practice of the invention.

Especially suitable as the titanate ester stabilizers of the invention are proprietary titanate ester compositions manufactured under the trade name "Tyzor" by DuPont de Nemours & Co., Inc. Preferred "Tyzor" titanate esters are those sold in the 100% form rather than as solutions, e.g. in a lower aliphatic alcohol, for example, "Tyzor" TBT (tetrabutyl titanate), Tyzor TPT (tetraisopropyl titanate), and Tyzor OG (tetraoctylene glycol titanate ester).

In preparing the titanate ester-stabilized-bisphenol compositions of the invention as little as about 0.1 mole percent, preferably from about 0.1 to about 3 mole percent of the titanate ester based on the moles of the bisphenol is employed. An especially good result is generally obtained in employing about 1 to about 3 mol percent of the titanate ester stabilizer, based on the mols of the bisphenol in the stabilized composition. While a proportion of the titanate ester stabilizer of 5 mol percent or more can be used, a proportion of ester stabilizer of more than 10 mole percent, while effective, may prove uneconomical, and hence is desirably avoided.

The preparation of the stabilized bisphenol compositions of the invention can be achieved by simple mechanical agitation of the mixture of the titanate ester stabilizer additive and the molten bisphenol e.g. by agitation of the mixture with a magnetically operated stirring bar.

In general, the present stabilizer titanate ester additives form homogeneous mixtures on blending with the molten bisphenol substrate and are apparently solutions of the stabilizer ester additive in the bisphenol.

The stabilized bisphenol compositions of the invention are eminently suitable as monomer precursors for manufacture of linear aromatic polyesters comprising bisphenol and dicarboxylic acid components, for example, by the polyesterification techniques described in the aforementioned U.S. Pat. No. 4,126,602 and British Pat. No. 924,607 and Ser. No. 198,979, filed Oct. 21, 1980, the disclosure of which is incorporated herein by reference. These polyesterification techniques include melt, i.e. transesterification polymerization techniques, such as transesterification of the bisphenol with a diaryl ester of the dicarboxylic acid wherein the aryl group is of the benzene or naphthalene series and is of 6 to 20 carbon atoms, as well as solution polymerization techniques including interfacial polymerization techniques. In melt polymerization processes, also described in J. C. Rosenfeld, copending U.S. application Ser. No. 128,743, filed Mar. 10, 1980; J. A. Pawlak et al., copending U.S. application Ser. No. 198,980, filed Oct. 21, 1980; and in G. M. Kosanovich et al., copending U.S. application Ser. No. 128,742, filed Mar. 10, 1980; Ser. No. 198,979, filed Oct. 21, 1980; and Ser. No. 232,929, filed Feb. 9, 1981, (said applications being incorporated herein by reference for their disclosures), the use of the present stabilized bisphenol composition is of special advantage. This is so since the present bisphenol composition contains as stabilizer the titanate ester which is a known transesterification catalyst for the melt polymerization of the bisphenol to prepare the aforementioned bisphenol dicarboxylic acid polyester.

The stabilized bisphenol compositions of the invention may also be employed effectively for the preparation of bisphenol epoxy compounds and the epoxy polymers prepared therefrom, in accordance with known polymerization techniques.

The following examples further illustrate the various aspects of the invention but are not intended to limit it. Various modifications can be made in the invention without departing from the spirit and scope thereof. Where not otherwise specified in this specification and claims, temperatures are given in degrees centigrade, and all parts and percentages are by weight.

EXAMPLE 1 (Control)

In a 250 ml. three necked flask equipped with a thermometer, a nitrogen gas inlet, a drying column for the nitrogen, a vertical condenser, a Dean-Stark trap and a magnetic stirring bar agitator is immersed in a silicone oil bath. The flask is charged with 50 g. (0.22 mol) of bisphenol A.

The flask containing the bisphenol composition is purged of air by a stream of dry nitrogen gas. The mixture is maintained at 250° for 24 hours. Weighed samples of the heated composition are withdrawn from the flask after 2 hour, 4 hour, and 24 hour periods of heating. Any distilled phenol decomposition product which has condensed on the walls of the condenser at the end of the aforementioned time periods is melted and allowed to flow back into the flask before the sample is withdrawn from the flask.

Each sample is allowed to cool to ambient temperature. The sample is then analyzed by gas-liquid chromotography to determine the weight percent concentration of phenol produced in the sample mixture during heating of the bisphenol. The weight percent concentration of phenol is based on the weight of the bisphenol composition charged to the flask. These results are set forth in the Table below.

In the Table the percentage concentrations of the phenol decomposition product in the samples are compared.

EXAMPLE 2

The procedure of Example 1 is repeated substantially as described except that the bisphenol A charged to the flask is admixed with about 0.0022 mol (corresponding to about one mol percent based on the bisphenol A charged) of tetra-isopropyl ortho titanate ester, a pale yellow liquid, manufactured under the designation TYZOR TPT by Du Pont de Nemours and Co., Inc. The results of this example are compared with the corresponding results of Example 1 in the Table below.

EXAMPLE 3

The procedure of Example 2 is repeated substantially as described except that the aliphatic titanate ester charged is tetra-n-butyl ortho titanate, a pale yellow liquid, manufactured under the designation TYZOR TBT by DuPont de Nemours and Co., Inc. The results of this example are compared with the corresponding results of the preceeding examples in the Table below.

EXAMPLE 4

The procedure of Example 2 is repeated substantially as described except that the titanate ester additive employed is a tetra-octylene glycol ortho titanate ester of the formula:

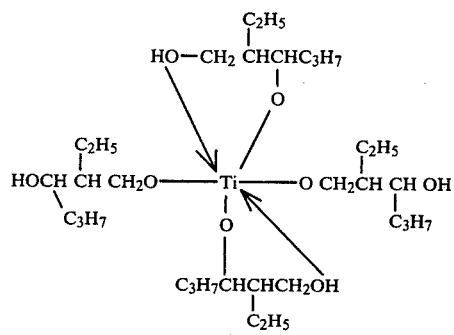

This ester, which is a pale yellow liquid, is manufactured under the designation TYZOR OG by DuPont de Nemours and Co., Inc. The results of this example are compared with the corresponding results of the preceeding examples in the Table below.

EXAMPLE 5 (Comparative)

The procedure of Example 2 is repeated substantially as described except that as the titanate-ester additive there is employed about 0.0018 mol of the ortho titanate ester of triethanolamine and propyl alcohol of the formula:

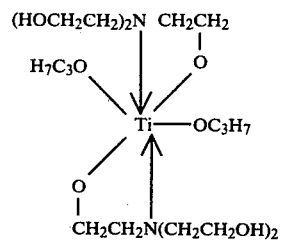

which is charged as an 80% solution in isopropyl alcohol. The alcoholic titanate ester solution, which is a pale yellow liquid, is manufactured under the designation TYZOR TE by DuPont de Nemours and Co., Inc. The results of this example are compared with the corresponding results of the preceeding Examples in the Table below.

TABLE

| Example: | Additive | After 2 Hours of Heating | | After 4 Hours of Heating | | After 24 Hours of Heating | |
|---|---|---|---|---|---|---|---|
| | | Mols Phenol in Heated Composition | Wt. Percent Phenol Based on Bisphenol Charged | Mols Phenol in Heated Composition | Wt. Percent Phenol Based on Bisphenol Charged | Mols Phenol in Heated Composition | Wt. Percent Phenol Based on Bisphenol Charged |
| 1(Control) | None | 0.0022 | 0.42 | 0.0062 | 1.16 | 0.061 | 11.51 |
| 2 | TYZOR TPT | None Detected | 0 | None Detected | 0 | $3.5 \times 10^{-4}$ | 0.065 |
| 3 | TYZOR TBT | — | Less than 0.1 | $6.9 \times 10^{-4}$ | 0.13 | 0.0081 | 1.52 |
| 4 | TYZOR OG | $3.2 \times 10^{-4}$ | 0.06 | 0.0017 | 0.32 | 0.021 | 3.96 |
| 5(comparative) | TYZOR TE | * | * | 0.0877 | 16.5 | — | — |

*Not determined since phenol in bisphenol composition after 4 hours of heating exceeded phenol produced in control after 4 hours of heating indicating that the amino-substituted titanate ester, TYZOR TE, is not a stabilizer for the bisphenol.

EXAMPLES 6–8

In these examples, three bisphenol A samples admixed with titanate ester stabilizers of the invention substantially as described in Examples 2-4 respectively, are maintained in the molten state for 2 to 4 hours under an inert atmosphere of dry nitrogen gas.

The molten bisphenol A compositions are then polymerized with a mixture of the diphenyl esters of isophthalic acid and terephthalic acid by a transesterification procedure substantially as described in the aforementioned copending U.S. patent application of G. M. Kosanovich et al., Ser. No. 232,929, to prepare a bisphenol A polyester of isophthalic and terephthalic acids.

The recovered polyester products of these examples are of excellent molecular weight and are molded to produce useful articles.

The invention has been described in the above specification and illustrated by reference to specific embodiments in the illustrative examples. However, it is to be understood that these embodiments are not intended to limit the invention since changes and modifications in the specific details disclosed hereinabove can be made without departing from the scope or spirit of the invention.

What is claimed is:

1. A thermally stabilized composition comprising a bisphenol and a stabilizing amount of a quarternary aliphatic ester of ortho titanic acid in a non-reactive environment for the bisphenol.

2. The composition of claim 1 wherein the bisphenol has the formula:

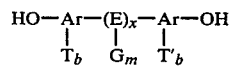

wherein Ar is aromatic, G is alkyl, haloalkyl, aryl, haloaryl, alkylaryl, haloalklaryl, arylalkyl, haloarylalkyl, cycloalkyl, or cyclohaloalkyl; E is divalent alkylene, haloalkylene, cycloalkylene, halocycloalkylene, arylene, or haloarylene, —O—, —S—, —SO₂—, —SO₃—, —CO—,

or GN<; T and T' are independently selected from the group consisting of halogen, G and OG; m is an integer from 0 to the number of replaceable hydrogen atoms on E; b is an integer from 0 to the number of replaceable hydrogen atoms on Ar, and x is 0 or 1.

3. The composition of claim 2 wherein x is 1.

4. The composition of claim 3 wherein the bisphenol is bisphenol A.

5. The composition of claim 4 wherein the titanate ester is derived from a hydrocarbon aliphatic alcohol having 1 to 12 carbon atoms.

6. The composition of claim 3 wherein the alcohol contains 1 to 8 carbon atoms.

7. The composition of claim 6 wherein the alcohol is a monohydroxy alcohol.

8. The composition of claim 4 wherein the titanate ester is derived from a branched chain alcohol.

9. The composition of claim 7 wherein the alcohol is a straight chain secondary alcohol.

10. The composition of claim 9 wherein the titanate ester is tetraisopropyl ortho titanate.

11. The composition of claim 7 wherein the alcohol is a straight chain primary alcohol.

12. The composition of claim 11 wherein the titanate ester is tetra-n-butyl ortho titanate.

13. The composition of claim 6 wherein the alcohol is a dihydroxy-branched chain alcohol.

14. The composition of claim 13 wherein the titanate ester is a tetra octylene glycol ortho titanate of the formula:

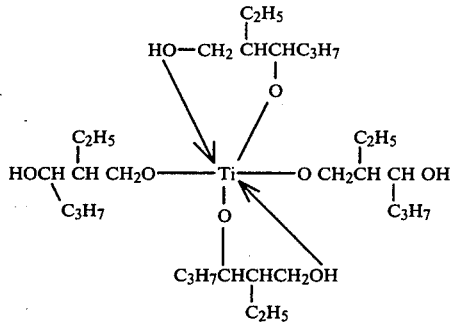

15. The composition of claim 4 wherein the titanate ester is present in an amount from about 0.1 to about 10 mole percent based on the bisphenol A.

16. The composition of claim 15 wherein the titanate ester is present from about 0.1 to about 3 mole percent based on the bisphenol A.

17. A method for preventing the thermal decomposition of a bisphenol which comprises incorporating into said bisphenol a stabilizing amount of a quarternary aliphatic ester of ortho titanic acid in a non-reactive environment for the bisphenol.

18. The method of claim 17 wherein the bisphenol has the formula:

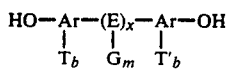

wherein Ar is aromatic, G is alkyl, haloalkyl, aryl, haloaryl, alkylaryl, haloalkylaryl, arylalkyl, haloarylalkyl, cycloalkyl, or cyclohaloalkyl; E is divalent alkylene, haloalkylene, cycloalkylene, halocycloalkylene, arylene, or haloarylene, —O—, —S—, —SO$_2$—, —SO$_3$—, —CO—,

or GN<; T and T' are independtly selected from the group consisting of halogen, G and OG; m is an integer from 0 to the number of replaceable hydrogen atoms on E; b is an integer from 0 to the number of replaceable hydrogen atoms on Ar, and x is 0 or 1.

19. The method of claim 18 wherein the bisphenol is bisphenol A.

20. The method of claim 19 wherein the titanate ester is derived from a hydrocarbon alcohol having 1 to 12 carbon atoms.

21. The method of claim 20 wherein the titanate ester is derived from a straight chain secondary alcohol.

22. The method of claim 21 wherein the ester is tetraisopropyl ortho titanate.

23. The method of claim 20 wherein the titanate ester is derived from a straight chain primary alcohol.

24. The method of claim 23 wherein the ester is tetra-n-butyl ortho titanate.

25. The method of claim 20 wherein the titanate ester is derived from a dihydroxy-branched chain alcohol.

26. The method of claim 25 wherein the titanate ester is tetra octylene glycol ortho titanate of the formula:

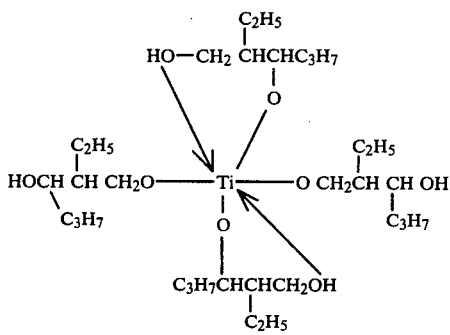

27. The method of claim 19 wherein the titanate ester is present in an amount from about 0.1 to about 10 mole percent based on the bisphenol A.

* * * * *